(12) United States Patent
Ding et al.

(10) Patent No.: US 11,555,049 B2
(45) Date of Patent: Jan. 17, 2023

(54) METHOD FOR SEPARATION AND PURIFICATION OF N-ACETYLGLUCOSAMINE

(71) Applicant: JIANGSU HARVERS BIOTECH CO., LTD., Zhenjiang (CN)

(72) Inventors: Chunhua Ding, Zhenjiang (CN); Wenjie Zhang, Zhenjiang (CN)

(73) Assignee: JIANGSU HARVERS BIOTECH CO., LTD., Zhenjiang (CN)

( * ) Notice: Subject to any disclaimer, the term of this patent is extended or adjusted under 35 U.S.C. 154(b) by 0 days.

(21) Appl. No.: 17/844,994

(22) Filed: Jun. 21, 2022

(65) Prior Publication Data

US 2022/0324896 A1    Oct. 13, 2022

Related U.S. Application Data

(63) Continuation of application No. PCT/CN2020/111610, filed on Aug. 27, 2020.

(30) Foreign Application Priority Data

Jun. 11, 2020 (CN) .......................... 202010527878.6

(51) Int. Cl.

| | | |
|---|---|---|
| C07H 1/06 | (2006.01) |
| B01D 15/18 | (2006.01) |
| B01D 15/36 | (2006.01) |
| B01D 21/01 | (2006.01) |
| B01D 21/26 | (2006.01) |
| B01D 25/12 | (2006.01) |
| B01D 37/02 | (2006.01) |
| B01D 37/03 | (2006.01) |
| B01D 61/02 | (2006.01) |
| B01D 69/02 | (2006.01) |
| C07H 5/06 | (2006.01) |

(52) U.S. Cl.
CPC ........... *C07H 1/06* (2013.01); *B01D 15/1821* (2013.01); *B01D 15/1871* (2013.01); *B01D 15/362* (2013.01); *B01D 15/363* (2013.01); *B01D 21/01* (2013.01); *B01D 21/262* (2013.01); *B01D 25/12* (2013.01); *B01D 37/02* (2013.01); *B01D 37/03* (2013.01); *B01D 61/025* (2013.01); *B01D 61/027* (2013.01); *B01D 69/02* (2013.01); *C07H 5/06* (2013.01); *B01D 2311/2623* (2013.01); *B01D 2311/2642* (2013.01); *B01D 2311/2649* (2013.01); *B01D 2311/2676* (2013.01); *B01D 2325/02* (2013.01); *B01D 2325/20* (2013.01)

(58) Field of Classification Search
CPC . C07H 1/06; C07H 5/06; C07H 13/02; B01D 21/01; B01D 37/03; B01D 15/1821; B01D 15/1871; B01D 15/362; B01D 15/363; B01D 21/262; B01D 25/12; B01D 37/02; B01D 61/025; B01D 61/027; B01D 69/02; B01D 2311/2623; B01D 2311/2642; B01D 2311/2649; B01D 2311/2676; B01D 2325/02; B01D 2325/20

See application file for complete search history.

(56) References Cited

FOREIGN PATENT DOCUMENTS

| | | |
|---|---|---|
| CN | 101365785 A | 2/2009 |
| CN | 103539244 A | 1/2014 |
| CN | 104788510 A | 7/2015 |
| CN | 105039464 A | 11/2015 |
| CN | 105543312 A | 5/2016 |
| CN | 105753913 A | 7/2016 |
| CN | 106008615 A | 10/2016 |
| CN | 106188167 A | 12/2016 |
| CN | 106831894 A | 6/2017 |
| CN | 106831895 A | 6/2017 |
| CN | 107354188 A | 11/2017 |
| CN | 108383883 A | 8/2018 |
| CN | 108484692 A | 9/2018 |
| JP | H0586399 B2 | 12/1986 |
| JP | S63273493 A | 11/1988 |
| JP | 2000281696 A | 10/2000 |
| JP | 2001292792 A | 10/2001 |
| JP | 5426099 B2 | 8/2009 |

(Continued)

OTHER PUBLICATIONS

Chmielowski et al., Biotechnol. J., 2007, 2, p. 996-1006. (Year: 2007).*

(Continued)

*Primary Examiner* — Jonathan S Lau
(74) *Attorney, Agent, or Firm* — IPro, PLLC

(57) ABSTRACT

The disclosure relates to a method for separation and purification of N-acetyl-glucosamine, and belongs to the technical field of biological engineering. In the disclosure, a raw material solution containing N-acetyl-glucosamine is obtained by microbial fermentation or by hydrolyzing the chitin. The raw material solution is subjected to flocculation pretreatment, and continuous centrifugation or pressure filtration is performed to remove suspended solids such as microorganisms, proteins and polysaccharides to obtain clear liquid. Double-stage ion exchange chromatography is performed to remove impurities such as charged organic molecules and inorganic salts. Membrane concentration is performed to efficiently remove water to improve the concentration of the target product. Spray drying or further evaporation concentration and crystallization are performed. Finally drying is performed to obtain an N-acetyl-glucosamine crystal of which the purity is more than 99%.

9 Claims, 1 Drawing Sheet

(56) References Cited

FOREIGN PATENT DOCUMENTS

| | | |
|---|---|---|
| JP | 2009191001 A | 8/2009 |
| WO | 03013435 A2 | 2/2003 |

OTHER PUBLICATIONS

English language EPO machine translation of CN 105543312 A, https://worldwide.espacenet.com/, accessed online on Sep. 20, 2022. (Year: 2022).*

* cited by examiner

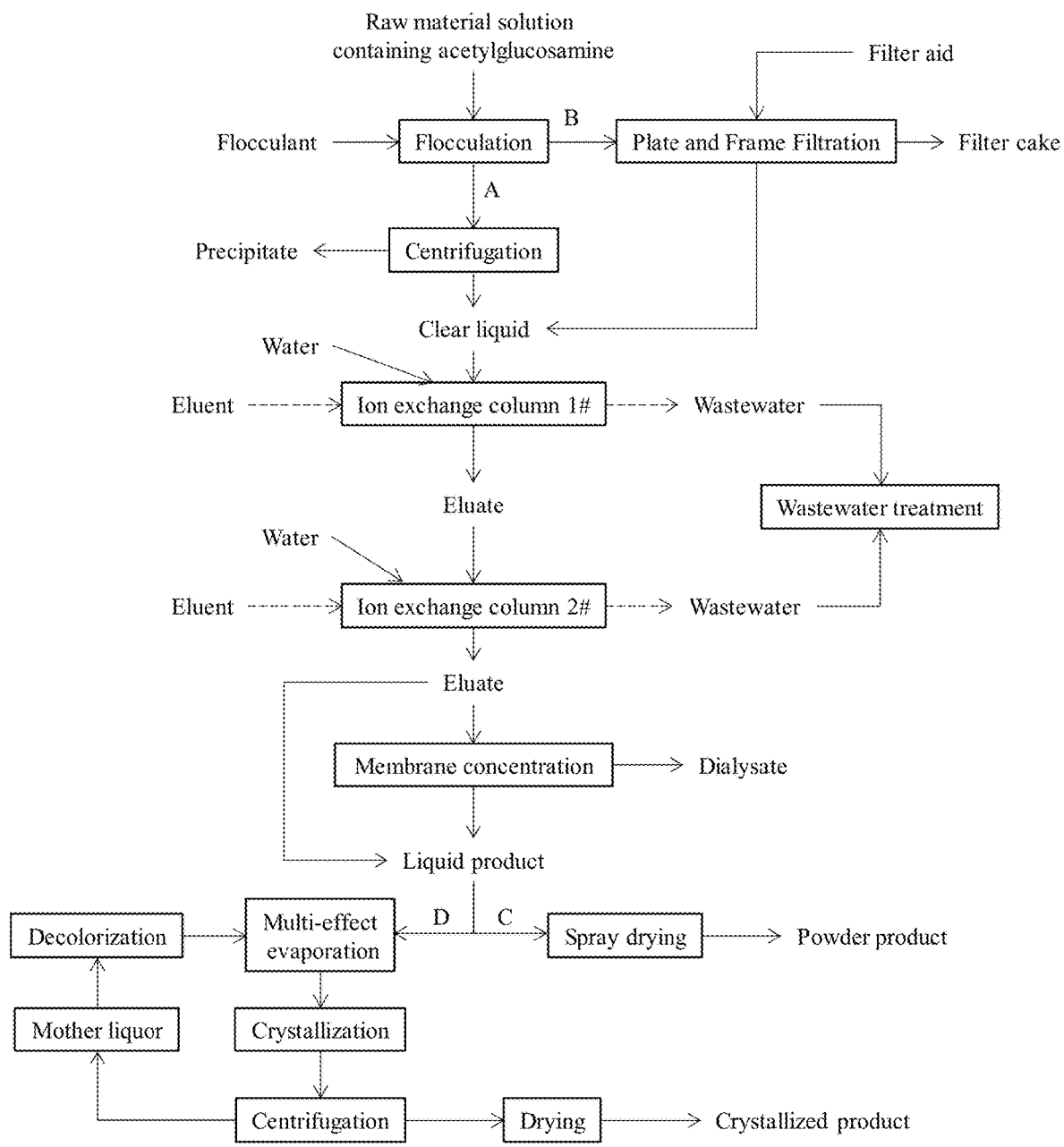

METHOD FOR SEPARATION AND PURIFICATION OF N-ACETYLGLUCOSAMINE

TECHNICAL FIELD

The disclosure relates to a method for separation and purification of N-acetyl-glucosamine, and belongs to the technical field of biological engineering.

BACKGROUND

N-acetyl-glucosamine (GlcNAc) is a glucose derivative, white powder. The solubility of the GlcNAc in 0° C. water is 140 g/L, and the GlcNAc is insoluble in organic solvents such as ethanol and propanol. The GlcNAc has stable physical and chemical properties, and the melting point of the GlcNAc is about 200° C. The GlcNAc is one of basic composition units of chitin. The GlcNAc widely exists in human bodies, animals, plants and microorganisms, and it plays important physiological and structural roles in various organisms. In human bodies, the GlcNAc is also an important precursor for the synthesis of glycosaminoglycans and bifidogenic factors. Clinically, the GlcNAc is a drug for the treatment of rheumatism and rheumatoid arthritis, and is also a precursor substance for the synthesis of N-acetyl-neuraminic acid. The GlcNAc can be used as a food antioxidant and a sweetener for diabetic patients. Therefore, the GlcNAc is widely used in food, medicine and cosmetic industries. At present, the synthesis of the GlcNAc is mainly based on chemical methods. Glucosamine hydrochloride is mainly obtained by acidic hydrolysis of chitin, and then, acetylation is performed with acetic anhydride to prepare the GlcNAc. Because the GlcNAc is widely used and has broad market prospects, it has aroused the interest of more and more researchers and market investors.

The GlcNAc exists in the cell walls of most yeasts and filamentous fungi and some bacteria. The GlcNAc is also an important precursor substance in glucosamine metabolic pathways of aforementioned microorganisms, and plays a crucial role in the cell growth and metabolism of microorganisms. The GlcNAc and glucosamine (GlcN) have important functions in repairing and maintaining human cartilage tissue health. The ability of the human body to synthesize and metabolize the GlcNAc and GlcN decreases with aging. Therefore, supplementation of the GlcNAc and GlcN can effectively prevent the human cartilage injury, and help to repair the injured cartilage and maintain the cartilage health.

At present, methods for producing GlcNAc are mainly divided into three categories: chemical methods, enzymatic methods and microbial methods. For natural raw materials such as shrimp and crab shells and fungal cell walls, impurities such as proteins, lipids and calcium carbonate in the raw materials need to be removed to obtain chitin, and then, the chitin is subjected to acidic hydrolysis or enzymatic hydrolysis to obtain a GlcNAc monomer. Raw materials such as shrimp and crab shells are limited by seasons and geographical conditions. When the chemical method is used for producing the GlcNAc, a large amount of inorganic acid needs to be consumed, which has the disadvantages of large energy consumption and serious environmental pollution. Furthermore, due to the presence of allergens in biological raw materials such as shrimps and crabs, it may cause allergic reactions in some people. Fungal cell walls also contain a relatively small amount of chitin which is closely combined with other components of the cell walls, such as proteins, other polysaccharides and lipids, and the separation and extraction processes are complicated. These problems limit the production of the GlcNAc by the chemical method.

The enzymatic method is mainly to obtain GlcNAc through the specific hydrolysis of chitin by chitinase, and the enzymes involved mainly include endochitinase, exochitinase and β-N-acetylhexosaminidase. The enzymatic method has the characteristics of less environmental pollution and low energy consumption. However, the hydrolysis reaction process involves the synergistic action of multiple enzymes, so the process is complicated and difficult to control. The high cost of enzymes production also limits the large-scale application of the enzymatic method in production of the GlcNAc.

With the rapid development of genetic engineering, metabolic engineering and synthetic biology, the technology for producing GlcNAc by recombinant microorganisms has been rapidly developed. By use of microorganisms such as recombinant *Escherichia coli* and recombinant *Bacillus subtilis*, the GlcNAc can be directly biosynthesized from glucose, and the product concentration can even exceed 100 g/L, which lays a good foundation for large-scale industrialization of the GlcNAc. The method for producing the GlcNAc by fermentation has the following advantages: (1) the conversion ratio of raw materials to products is high, and the cost of the raw materials is low; (2) the concentration of the fermented product is high, and the material consumption and energy consumption in the production process are relatively low; (3) the fermentation process is not affected by seasons, and the production cycle is short, thereby being suitable for large-scale production; and (4) chemical hydrolysis or enzymatic hydrolysis is not needed, the environmental pollution is small, and the cost can be greatly reduced. Therefore, this production path has received more and more attention.

Since the types, compositions and contents of target components and impurities in different raw materials are different, corresponding GlcNAc extraction processes need to be developed individually for different GlcNAc extraction raw materials. At present, for the extraction of GlcNAc, whether using microbial fermentation broth or shrimp and crab shells as raw materials, the reaction solution has the characteristics of complex components. Existing extraction methods often have the defects including low separation efficiency, high energy consumption and serious environmental pollution.

For example, "a method for deacetylated coupling adsorption and separation of D-glucosamine hydrochloride" in the Chinese patent ZL2016112278411 discloses an extraction process of deacetylated glucosamine. It adopts the process of removing microbial cells by microfiltration with ceramic membrane, decolorizing with activated carbon, removing impurities by cation and anion columns and performing concentration finally. However, the method has the defects of long extraction period, dilution of the target product during the removal of microorganisms by the microfiltration, large volume of the solid residue and wastewater, easy blockage of membrane modules, and high device investment and maintenance costs.

For another example, "a method for preparing GlcNAc based on microbial fermentation" in the patent application with an application number of CN2016100641584 discloses a process of pretreating fermentation broth through membrane filtration, activated carbon decolorization and chitosan flocculation, and then performing ion exchange, concentration and alcohol extraction, so as to obtain the GlcNAc. However, the method has the defects including complicated process route, large organic solvent consumption, high energy consumption, explosive solvent risk.

For yet another example, "a method for preparing high-purity GlcNAc" in the patent application with an application number of CN2018103088811 discloses an extraction method capable of removing impurities by a ceramic ultrafiltration membrane and performing activated carbon decolorization, electrodialysis desalination, evaporation concentration and crystallization, and vacuum drying. The raw material used in the method is the crude extract which comes from the extraction process of GlcNAc, and the product purity in the raw material is relatively high. The extraction process has the defects including large volume of the solid residue and wastewater, easy blocking of membrane components, and high device investment and maintenance costs.

SUMMARY

In view of the defects in the prior art such as high device investment, high energy consumption and serious environmental pollution in an extraction process, the disclosure provides an environment-friendly method for separation and purification of N-acetyl-glucosamine. The method takes fermentation broth containing N-acetyl-glucosamine or enzymatic hydrolysate of chitin as a raw material, and can efficiently extract and obtain N-acetyl-glucosamine solid powder and/or high-purity crystals.

An objective of the disclosure is to provide a method for preparing N-acetyl-glucosamine. The method takes a solution containing N-acetyl-glucosamine as a raw material, and sequentially performs flocculation, solid-liquid separation, double-stage ion exchange chromatography and drying, so that N-acetyl-glucosamine crystals with a purity greater than or equal to 99% may be obtained, and a high-purity N-acetyl-glucosamine concentrated solution or suspension with a concentration of 20-50% may also be obtained.

In an implementation mode, the method includes the following steps:

(1) adding a flocculant to a solution containing N-acetyl-glucosamine for flocculation;

(2) performing solid-liquid separation on the solution after the flocculation in step (1) to obtain clear liquid and solid waste;

(3) performing ion exchange chromatography on the clear liquid after the solid-liquid separation in step (2), wherein the ion exchange is double-stage ion exchange chromatography, including an ion exchange column 1 # and an ion exchange column 2 #; and (4) performing concentration treatment on the solution after the ion exchange chromatography in step (3), and then, drying the liquid product after the concentration; or directly drying the solution after the ion exchange chromatography in step (3).

In an implementation mode, the method takes a solution containing N-acetyl-glucosamine as a raw material solution, and performs separation and purification according to the following steps:

(1) adding a flocculant to the raw material solution containing N-acetyl-glucosamine for flocculation;

(2) performing solid-liquid separation on the solution after the flocculation in step (1) to obtain clear liquid and solid waste;

(3) performing ion exchange chromatography on the clear liquid after the solid-liquid separation in step (2), wherein the ion exchange is double-stage ion exchange chromatography, including an ion exchange column 1 # and an ion exchange column 2 #, and the polarity of the ion exchange column 1 # is opposite to the polarity of the ion exchange column 2 #; and (4) drying the solution after the ion exchange chromatography in step (3) to obtain an N-acetyl-glucosamine solid product; or concentrating the solution after the ion exchange chromatography in step (3) to obtain a high-purity N-acetyl-glucosamine liquid product with a concentration of 20-50%, and then, drying the product after the concentration.

In an implementation mode, the solid-liquid separation can use continuous centrifugation or pressure filtration; and the pressure filtration uses plate and frame pressure filtration.

In an implementation mode, the double-stage ion exchange chromatography uses ion exchange resin to adsorb impurities, and collects the liquid being not adsorbed by the ion exchange resin and flowing out.

In an implementation mode, the solution containing N-acetyl-glucosamine in step (1) may be obtained by microbial fermentation, or obtained by enzymatic hydrolysis of biological raw materials containing chitin, or obtained by chemical hydrolysis of raw materials containing chitin.

In an implementation mode, the flocculant used in step (1) is a food-safe organic flocculant, may also be a food-safe inorganic flocculant, or may be one or a combination of two or more selected from polyacrylamide, dimethylamine-epichlorohydrin copolymer, polyferric chloride, ferric chloride, ferric sulfate and ferrous sulfate.

In an implementation mode, a flocculant with a single component is added according to the following doses: the addition of the polyacrylamide is 0.01-0.3% of the dry weight of the biomass in the raw material, the addition of the dimethylamine-epichlorohydrin copolymer is 0.01-0.2% of the dry weight of the biomass, the addition of the polyferric chloride is 0.1-1.0% of the dry weight of the biomass, the addition of the ferric chloride is 0.1-0.9% of the dry weight of the biomass, the addition of the ferric sulfate is 0.1-1.0% of the dry weight of the biomass, and the addition of the ferrous sulfate is 0.2-2.0% of the dry weight of the biomass.

In an implementation mode, when a flocculant with two or more components is added, the addition of each component in the flocculant is 20-50% of the addition of the single component.

In an implementation mode, the solid-liquid separation in step (2) is operated through plate and frame pressure filtration or continuous centrifugation; the plate and frame pressure filtration may be performed by a box type plate and frame filter press or a diaphragm type filter press; and the continuous centrifugation may be performed by a disc centrifuge.

In an implementation mode, a filter aid needs to be added before the pressure filtration operation; the filter aid may be any one or a combination of two or more selected from diatomite, attapulgite, perlite and powdered activated carbon; and the total addition of the filter aid is 0.5-5% (w/v) of the raw material solution.

In an implementation mode, the double-stage ion exchange chromatography in step (3) uses a cation column-anion column system, or may use an anion column-cation column system, with fixed beds or simulated moving beds.

In an implementation mode, the double-stage ion exchange chromatography is performed by the simulated moving beds; the filler of the simulated moving bed is cation exchange resin or anion exchange resin, such as acidic cation exchange resin or basic anion exchange resin; the treatment temperature is 5-40° C., the feed flow rate is 2.0-10.0 BV/h, and the flow rate of eluents is 1.0-8.0 BV/h; and the eluents are a HCl solution with a concentration of 0.30-3.0 mol/L and a NaOH solution with a concentration of 0.50-3.0 mol/L respectively.

In an implementation mode, the concentration treatment in step (4) may use a reverse osmosis membrane or a nanofiltration membrane, the pore size of the nanofiltration membrane is 0.5-2 nm, and the molecular weight cut-off of the reverse osmosis membrane is 50-100 Da.

In an implementation mode, the concentration treatment is characterized in that the nanofiltration membrane is a ceramic membrane, and the operating pressure is 2-5 atm; and the reverse osmosis membrane is an organic roll type membrane or a ceramic membrane, and the operating pressure is 4-10 atm.

In an implementation mode, a concentrated solution after the membrane concentration treatment may be directly spray-dried to obtain N-acetyl-glucosamine powder, and the inlet air temperature of the spray drying is 150-300° C.

In an implementation mode, in step (5), the product after the concentration is first subjected to evaporation, then crystallization, centrifugation, and finally drying.

In an implementation mode, the evaporation may be single-effect evaporation, double-effect evaporation or triple-effect evaporation; and the temperature of the crystallization is 5-40° C.

In an implementation mode, the crystallized mother liquor after the centrifugation is subjected to decolorization, and the crystallized mother liquor after the decolorization is conveyed into an evaporation system again for recycling; and a method for decolorization is activated carbon adsorption decolorization or macroporous resin decolorization.

In an implementation mode, the drying is vacuum low temperature drying or flash drying; the temperature of the vacuum low temperature drying is 40-80° C., and the vacuum degree is 70-95 kPa; and the inlet air temperature of the flash drying is 150-300° C.

In an implementation mode, the multiple effect evaporation concentration treatment is characterized in that the multiple effect evaporation concentration is triple-effect evaporation, and the evaporation temperatures are 80° C., 70° C. and 60° C. respectively.

The disclosure also claims the applications of the method in preparation of N-acetyl-glucosamine or upstream and downstream products thereof.

Beneficial Effects

1. In the disclosure, by performing flocculation treatment, and optionally in combination with filter aids and adsorbents, macromolecular substances such as microbial cell, proteins and polysaccharides can be removed. Furthermore, some pigments can be removed at the same time. Compared with ceramic membrane-decolorization pretreatment, after the raw material is pretreated by the process of the disclosure, the concentration of the target product cannot be diluted, and the usage of activated carbon can be reduced by 30%, thereby being convenient for subsequent treatment.

2. In the disclosure, by using the double-stage ion exchange chromatography to treat the clear liquid after the solid-liquid separation, charged impurities can be efficiently removed, and pigments can be further removed. By using the simulated moving bed, the separation efficiency of ion exchange, the operation continuity and automation of the process can be improved. The consumption of resin can be reduced by 60%, the consumption of acid solution and alkali solution required for resin regeneration can be reduced by 40%, and the output of wastewater can be reduced by about 50%.

3. By using the reverse osmosis membrane or nanofiltration to concentrate the N-acetyl-glucosamine solution after the ion exchange treatment, the disclosure has the characteristics of high efficiency, energy saving and airtight operation. The spray drying used in the disclosure has the characteristics of simple operation, low device investment and easy control of sanitary conditions, and the purity of the obtained N-acetyl-glucosamine can reach 98%. Further, the multiple effect evaporation used in the disclosure has the characteristics of continuous production, low energy consumption, continuous crystallization and further decolorization. The product purity of the N-acetyl-glucosamine can be increased to be 99% or more, and thus, the product quality can be significantly improved.

BRIEF DESCRIPTION OF FIGURES

FIG. 1 shows extraction process routes of N-acetyl-glucosamine.

DETAILED DESCRIPTION

Technical Term

Eluate: the liquid solution that results from the ion exchange chromatography and contains the components which not be absorbed by the resin in the raw material solution. It is washed out with deionized water in the ion exchange process.

Example 1

N-acetyl-glucosamine was prepared according to branch A and branch C of the process routes in FIG. 1, and specific steps were:

(1) 50 m$^3$ of N-acetyl-glucosamine fermentation broth with a concentration of 50 kg/m$^3$ obtained by aerobic fermentation was collected in a fermentation broth storage tank. 20 L of a ferric sulfate solution with a concentration of 100 g/L and 25 L of a food-grade polyacrylamide solution with a concentration of 10 g/L were pumped into the fermentation broth storage tank. Stirring and mixing were performed completely, and then, flocculation was performed for 20 min.

(2) The solution after the flocculation in step (1) was continuously pumped into a disc centrifuge with a rotation speed of 12000 rpm. The collected clear liquid flowed into a clear liquid tank, and the precipitate was collected into a temporary storage tank.

(3) The clear liquid obtained in step (2) was sequentially pumped into an ion exchange column 1 #and an ion exchange column 2 #. The fillers in the ion exchange column 1 #and the ion exchange column 2 #were acidic cation exchange resin and basic anion exchange resin, respectively. The filler may also be basic anion exchange resin and acidic cation exchange resin, respectively. The flow rate was 4.0 BV/h, the eluate of the ion exchange column 2 #was collected into the storage tank, then the ion exchange column 1 #and the ion exchange column 2 #were washed with deionized water. The aforementioned eluates were all collected into the storage tank. The storage tank was configured to collect the eluate, and was used as a raw material solution storage tank for membrane concentration. A total of 51 m³ of eluate with an N-acetyl-glucosamine concentration of 46 kg/m³ was collected in the storage tank.

Optionally, according to the adsorption capacity of the resins in the columns, an HCl solution with a concentration of 1.0 mol/L and an NaOH solution with a concentration of 1.0 mol/L were flowed into the cation column and the anion column respectively so as to regenerate the ion exchange columns. The ion exchange columns were washed with deionized water to neutral pH, so that the ion exchange columns were in a standby state;

(4) The liquid in the storage tank collected in step (3), was pumped into a reverse osmosis membrane device and concentrated. The molecular weight cut-off of the reverse osmosis membrane was 50-100 Da and the operating pressure was 4-10 atm. 16.5 m³ of a concentrated solution with an N-acetyl-glucosamine concentration of 138 g/L was obtained after the concentration.

Optionally, the liquid collected in step (3) may also directly enter step (5) to be subjected to spray drying; and (5) the concentrated solution obtained in step (4) was subjected to spray drying. The inlet air temperature of the spray drying was 190° C., the feed flow rate was 2 m³/h, and 2230 kg of N-acetyl-glucosamine powder was obtained after drying. The purity of the N-acetyl-glucosamine powder was 99.2%, and the overall recovery ratio was 89.2%.

Example 2

N-acetyl-glucosamine was prepared according to branch B and branch C of process routes in FIG. 1, and specific steps were:

(1) 50 m³ of N-acetyl-glucosamine fermentation broth with a concentration of 50 kg/m³ obtained by aerobic fermentation was collected in a fermentation broth storage tank. 20 L of a ferric chloride solution with a concentration of 100 g/L and 25 L of a food-grade polyacrylamide solution with a concentration of 10 g/L were pumped into the fermentation broth storage tank. 500 kg of diatomite was added, stirring and mixing were performed, and then, flocculation was performed for 20 min.

(2) The solution after the flocculation in step (1) was pumped into a plate and frame filter press, when the pressure filtration was about to finish, 2 m³ of purified water was pumped in to wash the solid waste (filter cake) to obtain 50.2 m³ of filtrate with an N-acetyl-glucosamine concentration of 49 kg/m³, and the filtrate was collected into a clear liquid tank.

(3) The clear liquid in the clear liquid tank in step (2) was continuously pumped into a cation column of a simulated moving bed system of which the filler was strong acidic styrene type cation resin (001×7). The resulting eluate from the cation column was continuously pumped into an anion column of the simulated moving bed system of which the filler was strong basic styrene type anion resin (201×7). The flow rate was 5.5 BV/h; a total of 53 m³ of eluate with an N-acetyl-glucosamine concentration of 45.7 kg/m³ was collected into the storage tank. If the ion exchange resin had been adsorbed to saturation, flowed into an HCl solution with a concentration of 1.0 mol/L and an NaOH solution with a concentration of 1.0 mol/L continuously to regenerate the ion exchange columns. The ion exchange resins were then continuously washed with deionized water to neutral pH.

(4) The eluate liquid in the storage tank in step (3) was pumped into a reverse osmosis membrane device and concentrated. The molecular weight cut-off of the reverse osmosis membrane was 50-100 Da, and the operating pressure was 4-10 atm. 16.7 m³ of a concentrated solution was obtained after the concentration, and the N-acetyl-glucosamine concentration in the concentrated solution was 142 g/.

(5) The concentrated solution in step (4) was subjected to spray drying. The inlet air temperature of the spray drying was 150° C., the feed flow rate was 2 m³/h, and 2380 kg of N-acetyl-glucosamine powder was obtained after drying. The purity of the N-acetyl-glucosamine powder was 99.1%, and the overall recovery rate was 95.2%.

Example 3

The concentrated solution obtained in step (4) in Example 2 was treated according to a process route of a branch D in FIG. 1, and specific steps were:

(a) The solution of 142 g/L N-acetyl-glucosamine was pumped into a triple-effect evaporation device, and operating conditions were: the flow rate was 4 m³/h, the pressure of heating steam was 0.7 MPa, the vacuum degree of a triple-effect condenser was 90 kPa, the inlet temperature of cooling water was 8-15° C., and the concentration of the output product was 710 g/L.

(b) The output product in step (a) flowed into a crystallizer, and the crystallization temperature was controlled at 10° C. by jacket cooling.

(c) The crystal suspension resulted from the step (b) flowed into a centrifuge for solid-liquid separation; and (d) The mother liquor separated in step (c) was subjected to decolorization with an activated carbon column, and then, the decolorized mother liquor was returned into the storage tank before the triple-effect evaporation device. The crystal slurry obtained by centrifugation was conveyed into a flash dryer through a screw conveyer, the inlet air temperature of the flash drying was 180° C., the outlet air temperature of the flash drying was 80° C., and 2350 kg of an N-acetyl-glucosamine crystal was obtained. The purity of the N-acetyl-glucosamine powder was 99.5%, and the overall recovery rate was 94.0%.

Example 4

N-acetyl-glucosamine was prepared according to the branch B and branch C of process routes in FIG. 1, and specific steps were:

(1) 230 m³ of N-acetyl-glucosamine fermentation broth with a concentration of 110 g/L obtained by aerobic fermentation was collected in a fermentation broth storage tank. 100 L of a ferric sulfate solution with a concentration of 100 g/L and 100 L of a food-grade polyacrylamide solution with a concentration of 10 g/L were pumped into the fermentation broth storage tank. 1500 kg of attapulgite and 500 kg of powdered activated carbon were added. Agitation was performed for 20 min for uniformly mixing, and then, flocculation and decolorization were performed.

(2) The solution after the flocculation and decolorization in step (1) was pumped into a plate and frame filter press, the filtered initial liquid was returned to the fermentation broth storage tank. After the filtrate became clear, the obtained filtrate was collected into a clear liquid tank, and the water content of the obtained solid waste (filter cake) was about 62%.

(3) the clear liquid obtained by filtration in step (2) was continuously pumped into an ion exchange column 1 #(anion resin) of a simulated moving bed system, the eluate of the ion exchange column 1 #continuously flows into an ion exchange column 2 #(cation resin) of the simulated moving bed system. The feed flow rate of both the ion exchange column 1 #and the ion exchange column 2 #was 5.0 BV/h. The eluate of the ion exchange column 2 #was collected into the storage tank before the membrane concentration device. If the ion exchange resin was saturated, an HCl solution with a concentration of 1.0 mol/L and an NaOH solution with a concentration of 1.0 mol/L were respectively used to continuously regenerate the cation resin and the anion resin. The ion exchange columns were continuously washed with deionized water to neutral pH. The simulated moving bed performed automatic feeding, elution and regeneration of fillers of the columns. The filler of the anion column was strongly basic styrene type anion exchange resin (201×7), and the filler of the cation column was strongly acidic styrene type cation exchange resin (001×7).

(4) The liquid in the storage tank in step (3) was pumped into a ceramic nanofiltration membrane device and concentrated. The pore size of the ceramic nanofiltration membrane was 1 nm, and the operating pressure was 1.0-1.5 MPa. The N-acetyl-glucosamine concentration in 100 m³ of a concentrated solution after the concentration was 140 g/L.

(5) The concentrated solution in step (4) was subjected to spray drying. The inlet air temperature of the spray drying was 200° C., and the feed flow rate was 2 m³/h. 24.2 tons of N-acetyl-glucosamine powder was obtained after drying. The purity of the N-acetyl-glucosamine powder was 99.2%, and the overall recovery rate was 95.6%.

Example 5

On the basis of steps (1) to (4) in Example 4, N-acetyl-glucosamine was prepared according to the branch D of process routes in FIG. 1, and specific steps were:

(a) 100 m³ of the concentrated N-acetyl-glucosamine solution with a concentration of 140 g/L after the nanofiltration membrane device in step (4) in Example 4 was pumped into a triple-effect evaporation device. The operating conditions were: the feed flow rate was 8 m³/h, the pressure of heating steam was 0.7 MPa, the vacuum degree of the third condenser of the triple-effect evaporation was 90 kPa. The inlet temperature of cooling water was 8-15° C., and the concentration of the output product was 700 g/L;

(b) the output product in step (a) was conveyed to a crystallizer, and the crystallization temperature was controlled at 20° C. by jacket cooling of the crystallizer.

(c) A suspension produced by crystallization of the crystallizer in step (b) was separated in a centrifuge, the crystallized mother liquor was conveyed into an activated carbon column for decolorization. The operating temperature was 25° C., the flow rate was 2.0 m³/h, and the crystallized mother liquor after the decolorization was returned into the storage tank in front of the triple-effect evaporation device. The crystal slurry obtained by centrifugation was conveyed into a flash dryer through a screw conveyer. The air inlet temperature of the flash drying was 180° C., the outlet air temperature of the flash drying was 80° C., and 23.8 tons of an N-acetyl-glucosamine crystal was obtained. The purity of the N-acetyl-glucosamine powder was 99.5%, and the overall recovery rate was 94.1%.

Example 6

N-acetyl-glucosamine was prepared according to the branch A and branch C of the process routes in FIG. 1, and specific steps were:

(1) 50 m³ of N-acetyl-glucosamine fermentation broth with a concentration of 50 kg/m³ obtained by aerobic fermentation was collected in a fermentation broth storage tank. 20 L of a food-grade dimethylamine-epichlorohydrin copolymer solution with a concentration of 1.0% (w) and 18 L of a food-grade ferric chloride solution with a concentration of 10% were pumped into the fermentation broth storage tank. Stirring and mixing were performed completely, and then, flocculation was performed for 20 min.

(2) The solution after the flocculation in step (1) was pumped into a disc centrifuge with a rotation speed of 12000 rpm. 48.5 m³ of clear liquid with an N-acetyl-glucosamine concentration of 50 kg/m³ was collected into a clear liquid tank. The solid waste was collected into a temporary storage tank.

(3) the clear liquid collected in step (2) was continuously pumped into a cation column of a continuous moving ion exchange bed of which the filler was strongly acidic styrene type cation exchange resin (001×7) and an anion column of the continuous moving ion exchange bed of which the filler was strongly basic styrene type anion exchange resin (201×7) sequentially. The flow rate of the both columns was 2.5 BV/h, the cation column and the anion column were washed with deionized water, and 55 m³ of eluate with an N-acetyl-glucosamine concentration of 43 kg/m³ was collected. The eluate flowed into a storage tank in front of a reverse osmosis membrane device. HCl solution with a concentration of 1.0 mol/L and NaOH solution with a concentration of 1.0 mol/L were used to regenerate the cation column and the anion column respectively in the continuous moving ion exchange bed. Then, the ion exchange columns were washed with deionized water to neutral pH, and the ion exchange columns were in a standby state. The material consumption for extracting acetyl-glucosamine using various ion exchange procedures was shown in Table 1.

(4) The eluate collected in the storage tank in step (3) was directly subjected to spray drying. The inlet air temperature of the spray drying was 140° C., and the feed flow rate was 2 m³/h. 2295 kg of N-acetyl-glucosamine powder was obtained after drying. The purity of the N-acetyl-glucosamine powder was 99.3%, and the overall recovery rate was 91.8%.

Example 7

N-acetyl-glucosamine was prepared according to process routes in FIG. 1, and specific steps were:

(1) a solution containing N-acetyl-glucosamine was taken as a raw material, and a flocculant was added. The solution might be obtained by microbial fermentation, or obtained by enzymatic hydrolysis of biological raw materials containing chitin, or obtained by chemical hydrolysis of raw materials containing chitin.

The flocculant was an organic flocculant with food safety, might also be an inorganic flocculant with food safety, and was selected from one of polyacrylamide, dimethylamine-epichlorohydrin copolymer, polyferric chloride, ferric chloride, ferric sulfate and ferrous sulfate.

The additions of the flocculant were specifically as follows: the addition of the polyacrylamide was 0.01-0.3% of the dry weight of the biomass in the raw material. The addition of the dimethylamine-epichlorohydrin copolymer was 0.01-0.2% of the dry weight of the biomass. The addition of the polyferric chloride was 0.1-1.0% of the dry weight of the biomass. The addition of the ferric chloride was 0.1-0.9% of the dry weight of the biomass. The addition of the ferric sulfate was 0.1-1.0% of the dry weight of the biomass, and the addition of the ferrous sulfate was 0.2-2.0% of the dry weight of the biomass.

(2) The solution after the flocculation in step (1) was operated through plate and frame pressure filtration or continuous centrifugation. The plate and frame pressure filtration might be performed by a box type plate and frame filter press or a diaphragm type filter press. The continuous centrifugation might be performed by a disc centrifuge.

The filter residues after solid-liquid separation were used to prepare fertilizers, and the filtrate was used for the subsequent separation and extraction.

(3) The clear liquid obtained in step (2) was subjected to double-stage ion exchange chromatography. The double-stage ion exchange chromatography used a cation column-anion column system, or used an anion column-cation column system, with a fixed bed model or a simulated moving bed model.

The double-stage ion exchange chromatography was performed by the simulated moving bed. The filler of the simulated moving bed was cation exchange resin or anion exchange resin, such as strongly acidic cation exchange resin or strongly basic anion exchange resin. The operation temperature was 5-40° C., the feed flow rate was 2.0-10.0 BV/h, and the eluents flow rate was 1.0-8.0 BV/h. The eluents of the cation exchange resin and the anion exchange resin were a hydrochloric acid solution with a concentration of 0.30-3.0 mol/L and a NaOH solution with a concentration of 0.50-3.0 mol/L, respectively.

(4) The eluate after the ion exchange chromatography in step (3) was subjected to concentration by a reverse osmosis membrane or a nanofiltration membrane. The nanofiltration membrane was a ceramic membrane, the pore size of the nanofiltration membrane was 0.5-2 nm, and the operating pressure was 2-5 atm. The reverse osmosis membrane was an organic roll type membrane or a ceramic membrane, the molecular weight cut-off was 50-100 Da, and the operating pressure was 4-10 atm.

(5) the concentrated solution obtained in step (4) was subjected to vacuum drying or flash drying. The temperature of the vacuum low temperature drying was 40-80° C., and the vacuum degree was 70-95 kPa. The air temperature of the flash drying was 150-300° C. The overall recovery rate of the N-acetyl-glucosamine reached 90% or more, and the purity reached 99%.

Example 8

The specific implementation mode was the same as that in Example 7. The differences were as follows: the flocculant in step (1) was a combination of two or more selections from polyacrylamide, dimethylamine-epichlorohydrin copolymer, polyferric chloride, ferric chloride, ferric sulfate and ferrous sulfate. The addition of the flocculant was 0.02-0.7% of the dry weight of the biomass, and the addition of each component was specifically as follows:

The addition of the polyacrylamide was 0.005-0.15% of the dry weight of the biomass in the raw material, the addition of the dimethylamine-epichlorohydrin copolymer was 0.005-0.1% of the dry weight of the biomass, the addition of the polyferric chloride was 0.02-0.5% of the dry weight of the biomass, the addition of the ferric chloride was 0.02-0.45% of the dry weight of the biomass, the addition of the ferric sulfate was 0.02-0.5% of the dry weight of the biomass, and the addition of the ferrous sulfate was 0.04-0.4% of the dry weight of the biomass.

Other steps were the same as those in Example 7. The overall recovery rate of the N-acetyl-glucosamine reached 90% or more, and the purity reached 99%.

Example 9

The specific implementation mode was the same as that in Example 7. The differences were as follows: plate and frame pressure filtration was used in step (2). The filter aid was added before the pressure filtration operation, the filter aid may be one or a combination of two or more selections from diatomite, attapulgite, perlite and powdered activated carbon. The addition of the filter aid was 0.5-5% (w/v) of the raw material solution.

Other steps were the same as those in Example 7. The overall recovery rate of the N-acetyl-glucosamine reached 90% or more, and the purity reached 99%.

Example 10

The specific implementation mode was the same as that in Example 7. The differences were as follows: the concentrated solution obtained in step (4) was subjected to evaporation treatment and then crystallization at 5-40° C., wherein the evaporation might be the single-effect evaporation, double-effect evaporation or triple-effect evaporation.

The feed liquid after the crystallization was subjected to centrifugation. The crystallized mother liquor after the centrifugation was subjected to decolorization. The crystallized mother liquor after the decolorization was conveyed into an evaporation system again for recycling, wherein a method for decolorization was activated carbon adsorption decolorization or macroporous resin decolorization.

The crystal obtained after the centrifugation was dried to obtain a crystallized product of N-acetyl-glucosamine. The recovery ratio reached 90% or more, and the purity reached 99.5%.

Comparative Example 1

N-acetyl-glucosamine was prepared according to a method disclosed in a patent application with an application number of CN2016112278411, and specific steps were:

(1) 50 m$^3$ of N-acetyl-glucosamine fermentation broth with a concentration of 50 kg/m$^3$ obtained by aerobic fermentation was collected in a fermentation broth storage tank. Microbial cells were removed by filtration with a ceramic nanofiltration membrane. The pore size of the membrane was 5 nm. After the microbial cells were concentrated, 50 m$^3$ of pure water was added to dialyze the concentrated phase of the nanofiltration membrane, and a total of 90 m$^3$ of filtrate with an N-acetyl-glucosamine concentration of 25.3 kg/m$^3$ was collected. Meanwhile, 10 m$^3$ of waste residues with a high organic matter content were produced;

(2) the filtrate in step (1) was pumped into an adsorption column filled with activated carbon, and the dosage of the activated carbon was 2.5 kg/m$^3$.

(3) The solution absorbed by the activated carbon in step (2) was pumped into the first column filled with strongly acidic cation resin, the resulting eluate was then pumped into the second column filled with strongly basic anion resin. The flow rate was 4.5 BV/h, and 97 m$^3$ of eluate with an N-acetyl-glucosamine concentration of 22 kg/m$^3$ was collected. An HCl solution with a concentration of 1.0 mol/L and an NaOH solution with a concentration of 1.0 mol/L were used to regenerate the cation resin and the anion resin. The ion exchange columns were continuously washed with deionized water to neutral pH.

(4) the eluate treated in step (3) was subjected to triple-effect evaporation concentration, crystallization and drying according to the method in Example 3 to obtain 1990 kg of N-acetyl-glucosamine crystal. The overall recovery rate was 79.6%.

Comparative Example 2

N-acetyl-glucosamine was prepared according to a method disclosed in a patent application with an application number of 2018103088811, and specific steps were as follows:

(1) 50 m³ of N-acetyl-glucosamine fermentation broth with a concentration of 50 kg/m³ obtained by aerobic fermentation was collected in a fermentation broth storage tank. Microbial cells were removed by filtration with a ceramic ultrafiltration membrane, and the pore size of the membrane was 50 nm. After the microbial cells were concentrated, 50 m³ of pure water was added to dialyze the concentrated phase of the ultrafiltration membrane, and a total of 92 m³ of filtrate with a concentration of 25.5 kg/m³ was collected. Meanwhile, 8 m³ of waste residues with a high organic matter content were produced.

(2) The filtrate of the ceramic ultrafiltration membrane in step (1) was pumped into an adsorption column filled with activated carbon, and the dosage of the activated carbon was 2 kg/m³.

(3) The eluate after the adsorption and decolorization in step (2) was pumped into an electrodialysis membrane treatment system for desalination treatment. A total of 40 m³ of deionized water was added until the conductivity of the concentrated solution was lower than 50 μs/cm. The type of an electrodialysis membrane was a homogeneous ion exchange membrane. 17 m³ of a concentrated solution was obtained, and the product concentration was 126 kg/m³.

(4) The concentrated solution treated in step (3) was subjected to triple-effect evaporation concentration, crystallization and drying according to the method in Example 3 to obtain 1960 kg of N-acetyl-glucosamine crystal. The overall recovery rate was 78.4%.

The results of the acetyl-glucosamine extraction process using various solid-liquid separation methods were shown in Table 2.

TABLE 1

Material consumption for extracting N-acetyl-glucosamine using various ion exchange procedures

| Case number | Ion exchange procedure | Treatment volume of the raw material (m³) | GlcNAc concentration in raw material (kg/m³) | Filler loss (L/m³) | Usage of acidic and basic eluents (L/m³) |
|---|---|---|---|---|---|
| Example 1 | Fixed bed | 46.5 | 50 | 8 | 200 |
| Example 2 | Simulated moving bed | 50.2 | 49 | 1.5 | 90 |
| Example 6 | Continuous moving bed | 46.5 | 50 | 6 | 120 |

TABLE 2

The results of acetyl-glucosamine extraction process using various solid-liquid separation methods

| Case number | Solid-liquid separation method | Volume of solid waste (m³) | Consumption of pure water (m³) | GlcNAc concentration in clear liquid (kg/m³) | GlcNAc recovery rate (%) | Description of advantages and disadvantages |
|---|---|---|---|---|---|---|
| Example 1 | Flocculation and continuous centrifuge | 3.5 | 0 | 50 | 93% | A moderate amount of solid waste, less waste water, small volume of clear liquid, high concentration product, small device occupation, and relatively low recovery rate. |
| Example 2 | Flocculation and filter press | 1.8 | 2 | 49 | 98% | Less solid waste, less wastewater, small volume of the clear liquid, high concentration product, high recovery rate, simultaneous decolorization, and low device investment. |
| Comparative Example 1 | Ceramic nanofiltration membrane (5 nm) | 10 | 50 | 25.3 | 91% | Easy sanitary control, high automation, large amount of solid waste, large amount of pure water, large amount of waste water, low product concentration, slow filtration speed, higher equipment investment, and Consumable membrane modules. |
| Comparative Example 2 | Ceramic ultrafiltration membrane (50 nm) | 8 | 50 | 25.5 | 94% | Easy sanitary control, high automation, moderate equipment investment, large volume of solid waste, large consumption of pure water, large amount of waste water, low product concentration. |

Note:
the volume of raw material was 50 m³, and the acetyl-glucosamine concentration in the raw material solution was 50 g/L. Method for measuring chromaticity of clear liquid: 50 ml of a clear liquid was sampled and freeze-dried to obtain solid powder, the solid powder was diluted again to a concentration of 50 g/L GlcNAc, and then, chromaticity analysis was performed.

Although the disclosure has been disclosed above with preferred examples, it is not intended to limit the disclosure. Anyone familiar with this technology can make various changes and modifications without departing from the spirit and scope of the disclosure. Therefore, the protection scope of the disclosure should be defined by the claims.

What is claimed is:

1. A method for preparing N-acetyl-glucosamine, wherein the N-acetyl-glucosamine is prepared by taking a solution containing N-acetyl-glucosamine as a raw material solution according to the following steps:
   (1) adding flocculants to the raw material solution containing N-acetyl-glucosamine for flocculation, wherein the flocculants are food safety grade and used either as single component or in combination of two or more selected components from polyacrylamide, dimethylamine-epichlorohydrin copolymer, polyferric chloride, ferric chloride, ferric sulfate and ferrous sulfate;
   (2) performing solid-liquid separation on the solution after the flocculation in step (1) to obtain clear liquid and solid waste;
   (3) performing ion exchange chromatography on the clear liquid after the solid-liquid separation in step (2), wherein the ion exchange chromatography comprises double-stages column system of a cation column-anion column system or an anion column-cation column system in a device; and the form of the double-stages column system is an ion exchange fixed bed or an ion exchange simulated moving bed or an ion exchange continuous moving bed;
   (4) concentrating the solution after the ion exchange chromatography in step (3) to obtain a high-purity N-acetyl-glucosamine liquid product with a concentration of 20-50%; then, drying the product after the concentration, wherein the concentration treatment uses a reverse osmosis membrane or a nanofiltration membrane, the pore size of the nanofiltration membrane is 0.5-2 nm, and the molecular weight cut-off of the reverse osmosis membrane is 50-100 Da.

2. The method according to claim 1, wherein the raw material solution is a solution containing N-acetyl-glucosamine obtained by microbial fermentation or by hydrolyzing chitin; and the hydrolysis method comprises enzymatic hydrolysis or chemical hydrolysis.

3. The method according to claim 1, wherein the performing ion exchange chromatography comprises using ion exchange resin and adsorbing one or more impurities in the solution containing N-acetyl-glucosamine.

4. The method according to claim 3, wherein the adding mode of the flocculant in step (1) is (a) or (b):
   (a) a flocculant with a single component is added according to the following doses: the addition of the polyacrylamide is 0.01-0.3% of the dry weight of the biomass in the raw material, the addition of the dimethylamine-epichlorohydrin copolymer is 0.01-0.2% of the dry weight of the biomass, the addition of the polyferric chloride is 0.1-1.0% of the dry weight of the biomass, the addition of the ferric chloride is 0.1-0.9% of the dry weight of the biomass, the addition of the ferric sulfate is 0.1-1.0% of the dry weight of the biomass, and the addition of the ferrous sulfate is 0.2-2.0% of the dry weight of the biomass;
   (b) when a flocculant with two or more components is added, the addition of each component in the flocculant is 20-50% of the addition of the single component according to (a).

5. The method according to claim 1, wherein the solid-liquid separation in step (2) uses a device for plate and frame pressure filtration or continuous centrifugation; the device for plate and frame pressure filtration is a box type plate and frame filter press or a diaphragm type filter press; and the device for continuous centrifugation is a disc centrifuge.

6. The method according to claim 5, wherein a filter aid is added before the pressure filtration operation; the filter aid is any one or a combination of two or more selected from diatomite, attapulgite, perlite and powdered activated carbon; and the total addition of the filter aid is 0.5-5% of the raw material solution.

7. The method according to claim 5, wherein the solid-liquid separation in step (2) uses a device for plate and frame pressure filtration or continuous centrifugation; the device for plate and frame pressure filtration is a box type plate and frame filter press or a diaphragm type filter press; and the device for continuous centrifugation is a disc centrifuge.

8. The method according to claim 1, wherein a filler of a cation column or an anion column is acidic cation exchange resin or basic anion exchange resin; and
   the treatment temperature of the ion exchange chromatography is 5-40° C., the feed flow rate is 2.0-10.0 BV/h, and the flow rate of eluents is 1.0-8.0 BV/h.

9. The method according to claim 1, wherein the drying in step (4) is (a) or (b):
   (a) spray drying, vacuum low temperature drying or flash drying is performed; the inlet air temperature of the spray drying is 150-300° C.; the temperature of the vacuum low temperature drying is 40-80° C., and the vacuum degree is 70-95 kPa; and the inlet air temperature of the flash drying is 150-300° C.;
   (b) evaporation treatment and crystallization are performed subsequently, then the crystallized substance is dried; the evaporation is single-effect evaporation, double-effect evaporation or multiple effect evaporation; and the temperature of the crystallization is 5-40° C.

* * * * *